US011512305B2

(12) United States Patent
Medintz et al.

(10) Patent No.: US 11,512,305 B2
(45) Date of Patent: Nov. 29, 2022

(54) NANOPARTICLE-ATTACHED ENZYME CASCADES FOR ACCELERATED MULTISTEP BIOCATALYSIS

(71) Applicant: The Government of the United States of America, as represented by the Secretary of the Navy, Arlington, VA (US)

(72) Inventors: Igor L. Medintz, Springfield, VA (US); James N. Vranish, Mechanicsville, MD (US); Mario Ancona, Alexandria, VA (US); Kimihiro Susumu, Alexandria, VA (US); Sebastian A. Diaz, Washington, DC (US)

(73) Assignee: The Government of the United States of America, as represented by the Secretary of the Navy, Washington, DC (US)

( * ) Notice: Subject to any disclaimer, the term of this patent is extended or adjusted under 35 U.S.C. 154(b) by 553 days.

(21) Appl. No.: 15/840,283

(22) Filed: Dec. 13, 2017

(65) Prior Publication Data

US 2018/0171325 A1 Jun. 21, 2018

Related U.S. Application Data

(60) Provisional application No. 62/434,507, filed on Dec. 15, 2016.

(51) Int. Cl.

| | |
|---|---|
| ***C12N 11/18*** | (2006.01) |
| ***C12N 9/12*** | (2006.01) |
| ***C12N 9/04*** | (2006.01) |
| ***C12N 9/88*** | (2006.01) |
| ***C12N 9/92*** | (2006.01) |
| ***C12N 9/02*** | (2006.01) |
| ***C12N 9/90*** | (2006.01) |
| ***C12P 9/00*** | (2006.01) |

(52) U.S. Cl.

CPC ............ *C12N 11/18* (2013.01); *C12N 9/0006* (2013.01); *C12N 9/0008* (2013.01); *C12N 9/1205* (2013.01); *C12N 9/88* (2013.01); *C12N 9/90* (2013.01); *C12N 9/92* (2013.01); *C12P 9/00* (2013.01); *C12Y 101/01027* (2013.01); *C12Y 102/01012* (2013.01); *C12Y 207/01002* (2013.01); *C12Y 207/0104* (2013.01); *C12Y 207/01011* (2013.01); *C12Y 401/02013* (2013.01); *C12Y 503/01001* (2013.01); *C12Y 503/01009* (2013.01); *C12Y 504/02* (2013.01); *C07K 2319/21* (2013.01)

(58) Field of Classification Search

None

See application file for complete search history.

(56) References Cited

U.S. PATENT DOCUMENTS

| | | | |
|---|---|---|---|
| 8,642,356 | B2 | 2/2014 | Chung et al. |
| 2009/0143487 | A1 | 6/2009 | Dordick et al. |
| 2012/0070870 | A1 | 3/2012 | Way et al. |
| 2017/0174618 | A1 | 6/2017 | Cordova et al. |

OTHER PUBLICATIONS

Makriyannis T et al. Simultaneous Separation and Purifcation of Pyruvate Kinase and Lactate Dehydrogenase by Dye-Ligand Chromatography. 1993. Process Biochemistry. 28:179-185. (Year: 1993).*

Beeckmans S et al. Clustering of Sequential Enzymes in the Glycolytic Pathway and the Citric Acid Cycle. 1990. Journal of Cellular Biochemistry. 43:297-306. (Year: 1990).*

Misset O et al. Glycolytic enzymes of Trypanosoma brucei. 1986. European Journal of Biochemistry. 157, 441-453. (Year: 1986).*

W. Kang, Cascade biocatalysis by multienzyme-nanoparticle assemblies, 25 Bioconjugate Chem. Electronic Supplementary Information, 1-16, available at http://pubs.acs.org.*

Ansari et al. "Potential applications of enzymes immobilized on/in nano materials: A review." Biotechnol Adv. May-Jun. 2012;30(3):512-23.

K. S. Rabe, J. Müller, M. Skoupi, C. M. Niemeyer, Angew. Chem. Int. Ed. 2017, 56, 13574.

Kang et al., Bioconjugate Chemistry 2014, pp. 1387-1394.

Breger et al., ACS Nano 2015, pp. 8491-8503.

Kazenwadel et al., Analytical Methods 2015, pp. 4030-4037.

Vranish et al., Langmuir 2017, pp. 2901-2925.

International Search Report and Opinion dated Mar. 30, 2018 in PCT/US2017/066044.

Idan O, Hess H. Origins of activity enhancement in enzyme cascades on scaffolds. ACS Nano. Oct. 22, 2013;7(10):8658-65. doi: 10.1021/nn402823k.

Klein WP, Thomsen RP, Turner KB, Walper SA, Vranish J, Kjems J, Ancona MG, Medintz IL. Enhanced Catalysis from Multienzyme Cascades Assembled on a DNA Origami Triangle. ACS Nano. Nov. 21, 2019;. doi: 10.1021/acsnano.9b05746.

Kuzmak A, Carmali S, von Lieres E, Russell AJ, Kondrat S. Can enzyme proximity accelerate cascade reactions?. Sci Rep. Jan. 24, 2019;9(1):455. doi: 10.1038/s41598-018-37034-3.

Wheeldon I, Minteer SD, Banta S, Barton SC, Atanassov P, Sigman M. Substrate channelling as an approach to cascade reactions. Nat Chem. Apr. 2016;8(4):299-309. doi: 10.1038/nchem.2459.

Zhang Y, Tsitkov S, Hess H. Proximity does not contribute to activity enhancement in the glucose oxidase-horseradish peroxidase cascade. Nat Commun. Dec. 22, 2016;7:13982. doi: 10.1038/ncomms13982.

* cited by examiner

*Primary Examiner* — Paul J Holland

(74) *Attorney, Agent, or Firm* — US Naval Research Laboratory; Roy Roberts

(57) ABSTRACT

A nanoparticle (for example, quantum dot) serves as a substrate for immobilizing enzymes involved in consecutive reactions as a cascade. This results in a significant increase in the rate of catalysis as well as final product yield compared to non-immobilized enzymes.

4 Claims, 13 Drawing Sheets

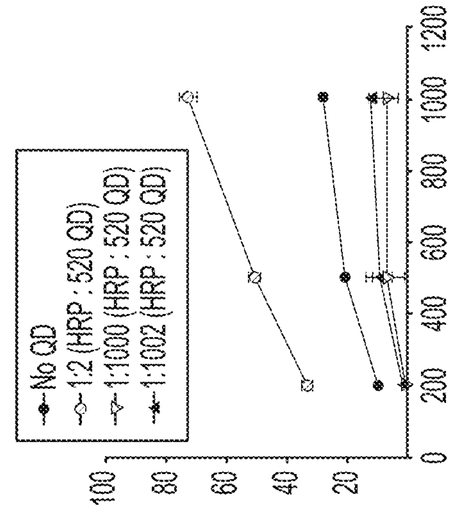
FIG. 3A
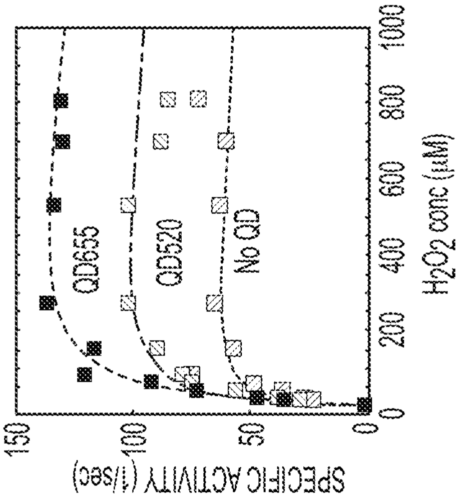
FIG. 3B
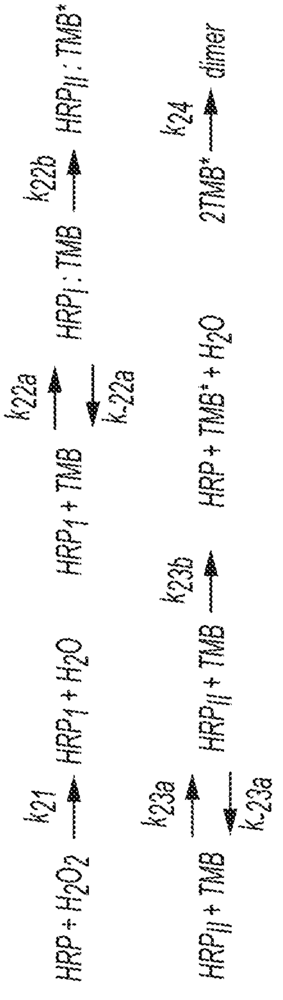
FIG. 3C
| KINETIC PARAMETERS DERIVED FROM MODELING | | | |
|---|---|---|---|
| | NO QD | QD 520 | QD 655 |
| $k_{21}$ | $2.1 \times 10^6$ | $2.1 \times 10^6$ | $2.1 \times 10^6$ |
| $k_{2na}$ | $4.6 \times 10^5$ | $4.6 \times 10^5$ | $4.6 \times 10^5$ |
| $k_{-2na}$ | $1.2 \times 10^7$ | $6.3 \times 10^6$ | $4.6 \times 10^6$ |
| $k_{2nb}$ | $2.1 \times 10^6$ | $2.1 \times 10^6$ | $2.1 \times 10^6$ |
FIG. 3D

GLUCOSE

D-GLUCONO-1,5-LACTONE 3, 3′,5 5′-TETRAMETHYLBENZIDINE (TMB)

TMB CHARGE TRANSFER COMPLEX (TMB PRODUCT)

PEP ADP PYRUVATE ATP

PYRUVATE NADH (ABSORBANCE @ 340 nm) LACTATE NAD+ (COLORLESS)

NANOPARTICLE-ATTACHED ENZYME CASCADES FOR ACCELERATED MULTISTEP BIOCATALYSIS

CROSS-REFERENCE TO RELATED APPLICATIONS

This Application claims the benefit of U.S. Provisional Application 62/434,507 filed on Dec. 15, 2016, the entirety of which is incorporated herein by reference.

BACKGROUND

Immobilized enzymes are of considerable interest for industrial and clinical purposes since immobilization allows for the reuse of enzymes, facile separation of enzymes and products, and often leads to enhanced physicochemical stability of the enzymes. However, immobilization of enzymes on large surfaces also leads to diminished activity of the bound enzyme. In contrast, immobilization of enzymes on nanoparticles (NPs) has been shown to often result in an increase in enzymatic activity. Among the wide variety of available NPs are quantum dots (QDs). These NPs are particularly useful to immobilize enzymes, since the enzyme can be easily attached to the ZnS surface shell via their display of a hexahistidine tag using metal affinity coordination with a dissociation constant of ~1 nM. NPs synthesized from gold or other noble metals or even any other material while displaying a surface nitrilotriacetic acid group coordinated to a requisite metal ion will also functional equally well. Although many enzymes have been shown to have enhanced activity on NPs, to date there does not appear to have been a demonstration of the applicability of this method of immobilization to a complex multistep enzymatic cascade.

BRIEF SUMMARY

The purpose of this invention is to take advantage of enzyme immobilization on metal-coated NPs in the context of an enzymatic cascade. Often multiple enzymatic steps are required in industrial processes in order to complete the transformation of reactants over multiple steps to their desired product. As described herein, the enhancement of a single NP-bound enzyme can be harnessed within an enzymatic cascade with other unbound enzymes, and binding of multiple enzymes to a NP can provide even further catalytic enhancement.

In one embodiment, an enzymatic cascade cluster includes a plurality of nanoparticles associated together as a cluster, wherein each nanoparticle is bound to a plurality of enzymes configured as an enzymatic cascade wherein the product of a first enzyme is the substrate of a second enzyme and so forth; wherein the enzymatic cascade comprises at least two different enzymes; and wherein the nanoparticles in the cluster are closely associated with one another such that, on average, each nanoparticle is separated from the nearest neighboring nanoparticle by a distance of no more than about one nanoparticle diameter.

Also contemplated is an embodiment wherein a single nanoparticle (not necessarily part of a cluster) is bound to the plurality of enzymes which form an enzymatic cascade.

In a further embodiment, an enzymatic cascade cluster includes a plurality of quantum dots (QDs) associated together as a cluster, wherein each nanoparticle is bound to a plurality of enzymes configured as an enzymatic cascade wherein the product of a first enzyme is the substrate of a second enzyme and so forth; wherein the enzymatic cascade consists of the enzymes glucokinase, phosphoglucose isomerase, phosphofructokinase, fructose-bisphosphate aldolase, triose phosphate isomerase, glyceraldehyde-3-phosphate dehydrogenase, and phosphoglycerate mutase, each enzyme incorporating a polyhistidine sequence associating the enzyme to the QD; and wherein the QDs in the cluster are closely associated with one another such that, on average, each QD is separated from the nearest neighboring QD by a distance of no more than about one QD diameter In another embodiment, a method of conducting a cascade reaction, providing a cascade cluster comprising a plurality of nanoparticles associated together as a cluster, wherein each nanoparticle is bound to a plurality of enzymes configured as an enzymatic cascade wherein the product of a first enzyme is the substrate of a second enzyme and so forth, wherein the enzymatic cascade comprises at least two different enzymes, and wherein the nanoparticles in the cluster are closely associated with one another such that, on average, each nanoparticle is separated from the nearest neighboring nanoparticle by a distance of no more than about one nanoparticle diameter; contacting the cascade cluster with a substrate of the first enzyme; and allowing a reaction to proceed so that each of the plurality of enzymes acts in succession to produce an end product, wherein the reaction is performed while minimizing stirring or mixing.

BRIEF DESCRIPTION OF THE DRAWINGS

FIG. 1A shows TMB product formation vs. time for 1 nM HRP samples without QD, with 1 equivalent of 655 nm emitting QDs solubilized with a CL4 surface ligand, and with 1 equivalent of 520 nm emitting QDs with CL4 (green). FIG. 1B shows results with HRP (1 nM) incubated with varying ratios of either 520 nm emitting QDs solubilized with CL4 or 655 nm-CL4. The activity was measured using 1 mM $H_2O_2$ as the substrate. The observed rates were compared to identical samples lacking QDs. FIG. 1C shows Michaelis-Menton measurements for activity of HRP loaded QDs with $H_2O_2$ as a substrate. HRP activity was measured for samples containing 1 nM HRP and varying concentrations of $H_2O_2$. The samples contained either no QD or 2 nM 655-CL4 or 2 nM 520-CL4.

FIGS. 3A-3D show that HRP kinetics are enhanced by QD binding via tetramethylbenze (TMB) accumulation near the QD surface. FIG. 3A shows results after HRP samples were preincubated with 2 equivalents of QD or without any QD. These samples were then diluted into wells that contained varying concentrations of TMB and either 1000 equivalents of QD or no QD. 1 mM $H_2O_2$ was added to initiate the reaction and the specific activity was recorded. FIG. 3B shows data from FIG. 1C fit using microscopic rate constants as detailed in FIGS. 3C and 3D. FIG. 3C shows the reaction scheme and microscopic rate constants for the HRP reaction cycle. FIG. 3D shows rate constants used to generate the curves in FIG. 3B. The rate constants for TMB dissociation were changed, which is consistent with an increase in the local TMB concentration at the NP surface.

FIG. 6C shows results of similar assays, except the assays were either kept stationary or rapidly shaken throughout the assay.

FIG. 8A illustrates chemical reactions carried out by a cascade of GOX and HRP. FIG. 8B is a diagram of a scheme where HRP is bound to a QD and receives its peroxide substrate from GOX which is unbound.

FIG. 9A illustrates chemical reactions carried out by a cascade of PykA and LDH. FIG. 9B is a diagram of a scheme where both PykA and LDH are bound to the same QD and the intermediate pyruvate is channeled between the two enzymes due to their colocalization.

DETAILED DESCRIPTION

Definitions

Figure 1C:
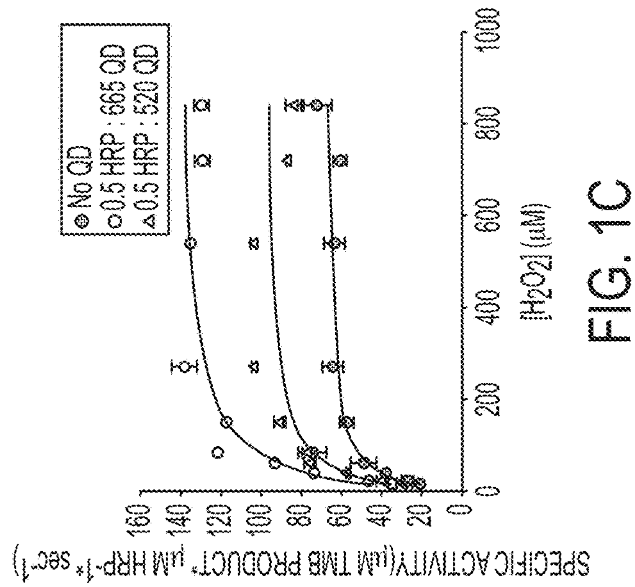
FIGS. 1A-1C show enhancement of horseradish peroxidase (HRP) reaction kinetics when HRP is bound to the quantum dot (QD) surface.

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used herein, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

The terms "semiconductor nanocrystal," "quantum dot," and "QD" are used interchangeably herein and refer to an inorganic crystallite of about 1 nm or more and about 1000 nm or less in diameter or any integer or fraction of an integer therebetween, preferably at least about 2 nm and about 50 nm or less in diameter or any integer or fraction of an integer therebetween, more preferably at least about 2 nm and about 20 nm or less in diameter (for example about 2, 3, 4, 5, 6, 7, 8, 9, 10, 11, 12, 13, 14, 15, 16, 17, 18, 19, or 20 nm). QDs are characterized by their relatively uniform nanometer size. A QD is capable of emitting electromagnetic radiation upon excitation (the QD is luminescent) and includes a "core" of one or more first semiconductor materials, with the core optionally surrounded by a "shell" of a second semiconductor material.

The term "nanoparticle" or "NP" as used herein includes the above-mentioned QDs in addition to other nano-scale and smaller particles such as metallic nanoparticles (e.g., nanoparticles comprising Ag, Au, Cu, Pd, Pt, and combinations thereof), carbon nanotubes, proteins, polymers, dendrimers, viruses, and drugs. A nanoparticle has a size of less than about 1 micron, optionally less than about 900, 800, 700, 600, 500, 400, 300, 200, 100, 80, 60, 50, 40, 30, 20, 10, 9, 8, 7, 6, 5, 4, 3, 2, or 1 nanometers. A nanoparticle may have various shapes such as a rod, a tube, a sphere, and the like. Nanoparticles may be made from various materials including metals, carbon (such as carbon nanotubes), polymers, and combinations thereof.

Overview

Enzymes that carry out consecutive reactions are of great interest as biochemical catalysts. The stability of enzymes can often be improved by immobilizing enzymes on a surface. Furthermore, many groups have demonstrated that co-localization of enzymes on a planar surface can sometimes improve the overall catalytic rate of the pathway.

As described herein, the overall kinetics of an enzymatic cascade that includes a nanoparticle (NP)-bound enzyme can be enhanced. A bound enzyme appears relatively unaffected by the presence of additional enzymes in solution, suggesting that this method can be resistant to fouling. Additionally, multiple enzymes that comprise a sequential enzymatic cascade can be immobilized onto a NP surface with the net result of a significant increase in the rate of catalysis as well as final product yield in comparison to equivalent non-NP controls. Furthermore, this results from a combination of enhanced stability of the bound enzymes, rate acceleration of the individual enzymes, and potential substrate channeling between bound enzymes. The large surface area of QDs and other NPs enables the binding of several enzymes simultaneously, and has allowed us the observation of catalytic enhancement of enzyme cascades that include 7 different enzymes, which perform 6 consecutive catalytic steps.

One or more enzymes can be immobilized on a nanoparticle using techniques known in the art (see References), for example by using enzymes that have been genetically modified to incorporate polyhistidine tags.

EXAMPLES

Standard laboratory techniques were used to perform these examples, for example as described in *Nanoscale,* 2017, 9, 5172-5187, incorporated herein by reference for the purposes of detailing methods for making and using the described nanoparticles.

Figure 1B:
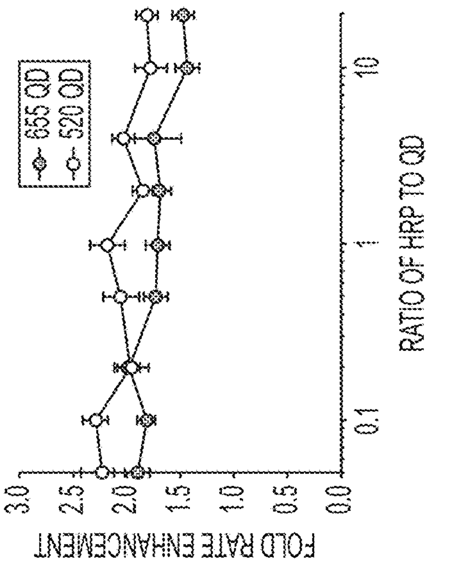
Figure 1A:
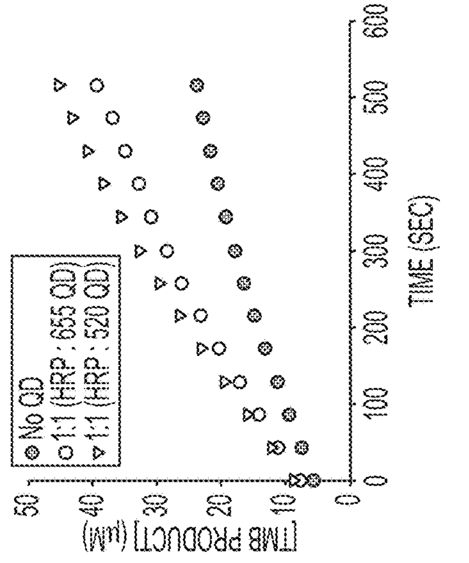
Figure 2:
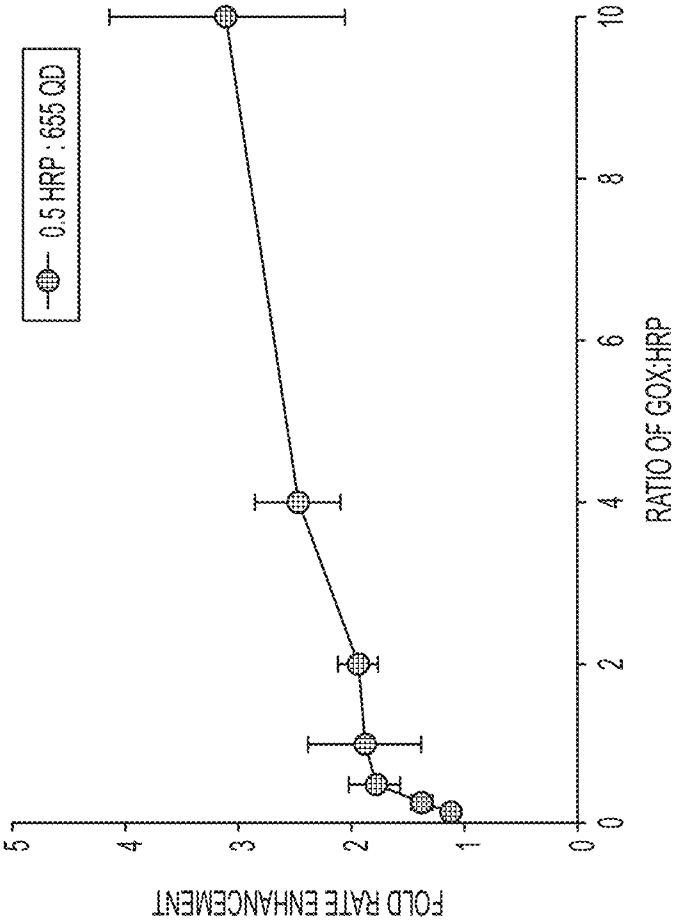
FIG. 2 shows the kinetics of a glucose oxidase (GOX)/HRP cascade are enhanced by binding HRP to a QD surface. The rate enhancement of HRP by 655-CL4 (2:1 ratio of QD to HRP) was measured using 20 mM glucose and varying ratios of GOX as $H_2O_2$ generators.
Figure 8A:
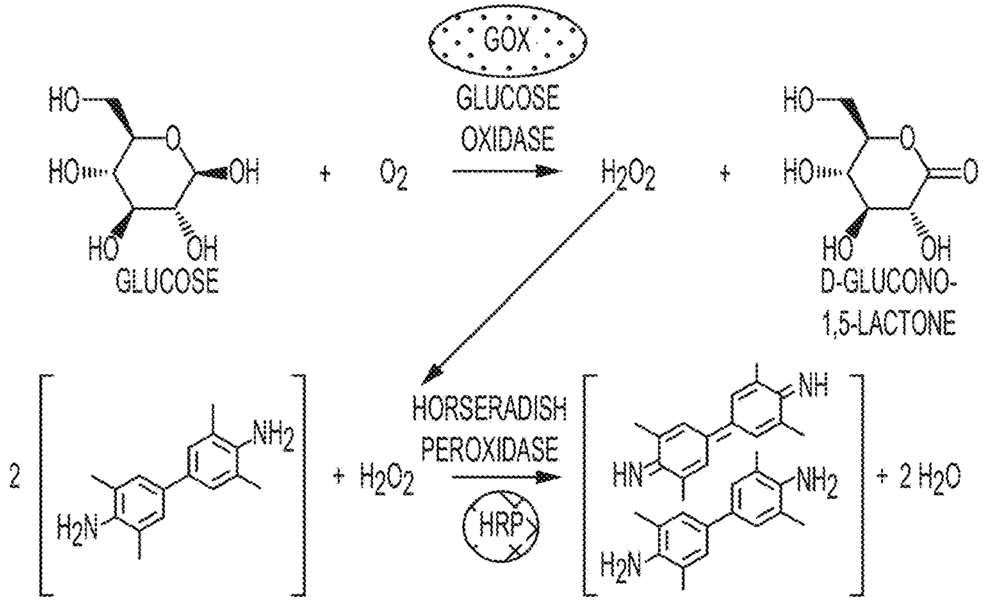
FIGS. 8A and 8B refer to combined reactions of glucose oxidase and horseradish peroxidase on a QD surface.
Figure 8B:
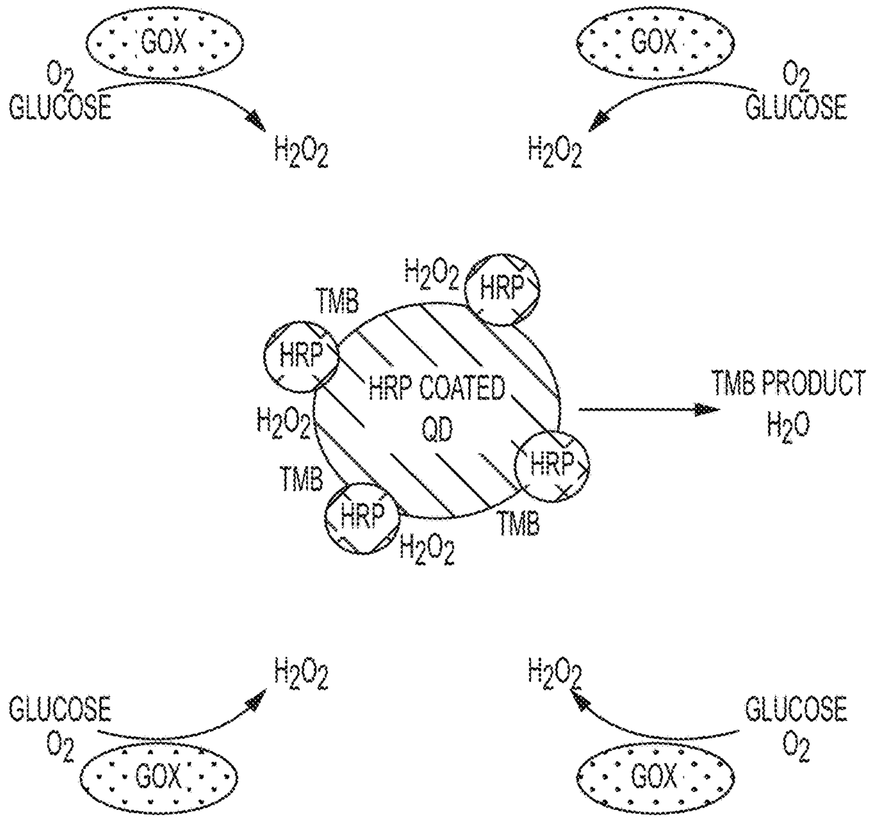

Initial efforts showed evidence for catalytic enhancement of two enzymatic cascades when bound to QDs: (1) beta-galactosidase, glucose oxidase (GOX), and horseradish peroxidase (HRP) and (2) GOX and HRP. An investigation was made in a system where HRP was bound to a QD and GOX was unbound (FIGS. 8A and 8B). In this case, QD-binding enhanced the activity of bound HRP (FIGS. 1A-1C). Furthermore, as the ratio of GOX to HRP increased in a combined reaction, the enhancement of bound HRP was observed in the overall reaction kinetics (FIG. 2). Further experiments and kinetic modeling both suggested that the enhancement in the kinetics of bound HRP could be due to substrate accumulation near the QD surface (FIGS. 3A-3D).

Figure 4:
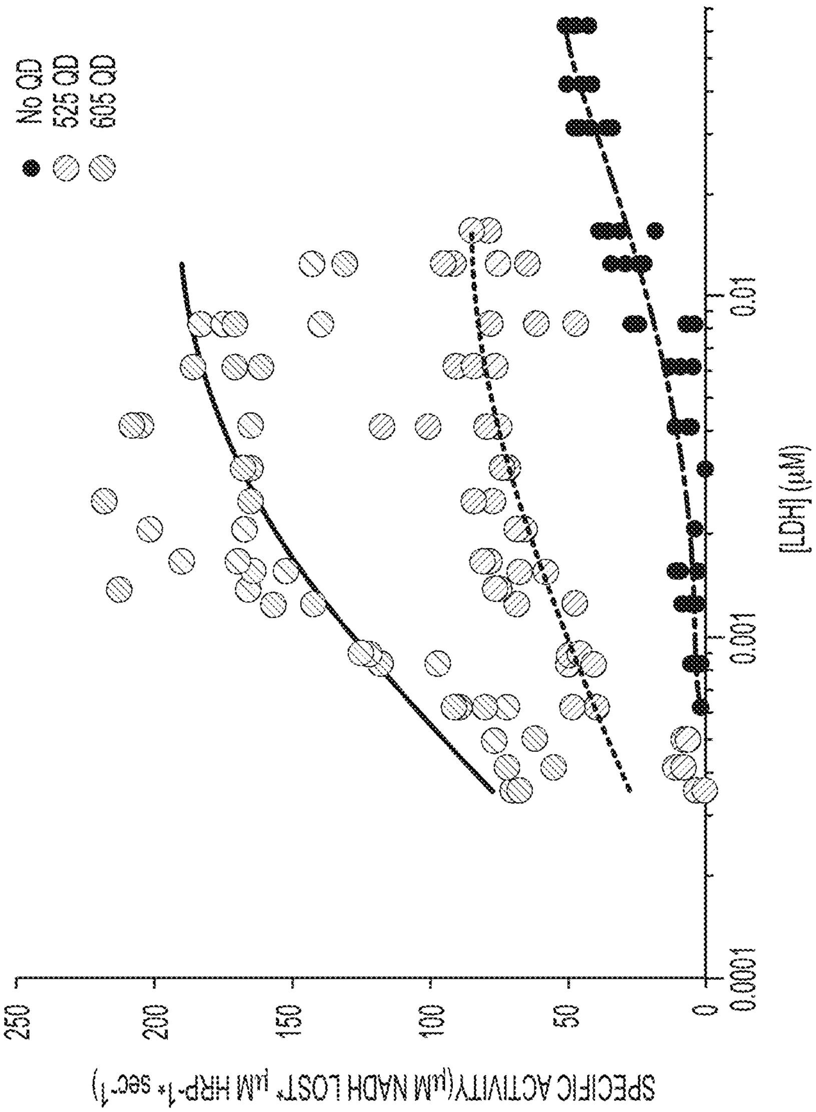
FIG. 4 shows LDH activity being enhanced on a QD surface by preserving the oligomeric state of LDH. The specific activity of LDH was measured either on or off two different sized QDs at varying concentrations of LDH (the ratio of LDH to QD was fixed). These studies reveal a concentration dependent deactivation of the enzyme, consistent with dissociation of the LDH tetramer. The dissociation constant shifts from 26 nM (for the sample lacking QD) to <1 nM for the two samples bound to QDs.
Figure 5:
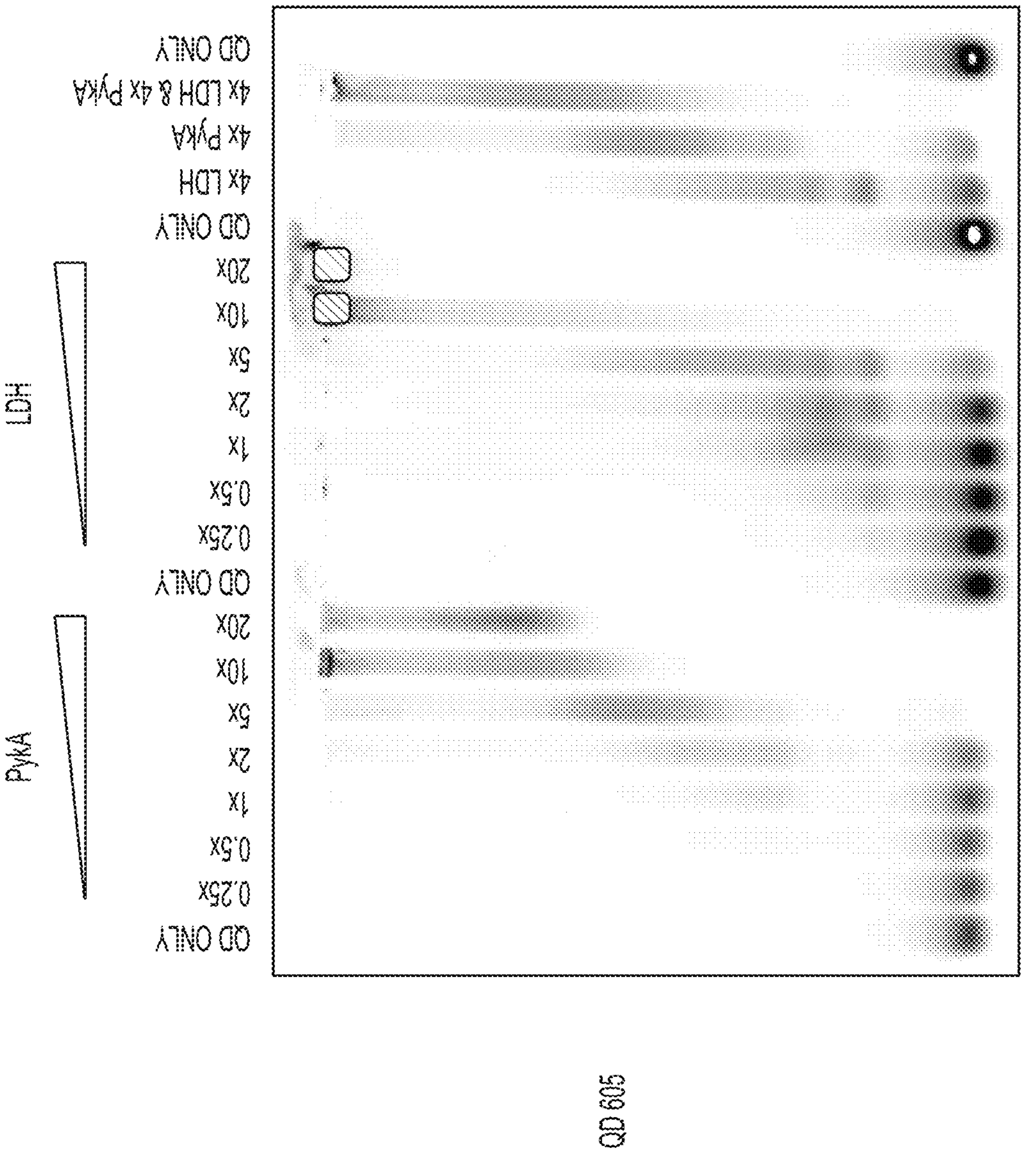
FIG. 5 shows that PykA and LDH can simultaneously bind to a QD surface. An agarose gel was run in TBE buffer with varying ratios of either LDH or PykA to QD. Incubating the QD with 4 equivalents of LDH and PykA produced a greater shift than incubation with 4 equivalents of either enzyme alone, suggesting that they bind simultaneously to the surface.
Figure 6C:
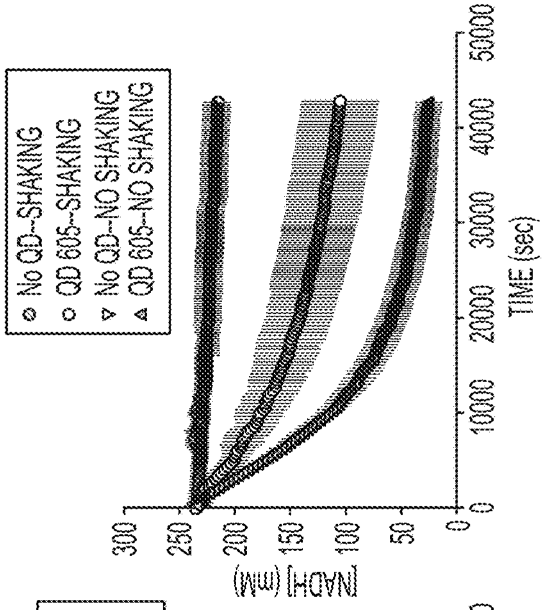
FIGS. 6A-6C shows that the combined activity of PykA and LDH is enhanced by QD binding. For FIGS. 6A and 6B, PykA and LDH were mixed in various ratios and incubated either with or without QD. The concentration of the substrate NADH was monitored over time (it was the limiting reagent in these reactions). Notably, enzymes on the QD are still active at 15000 seconds (B) whereas the enzymes off the QD (A) are inactive at the same time point.
Figure 6B:
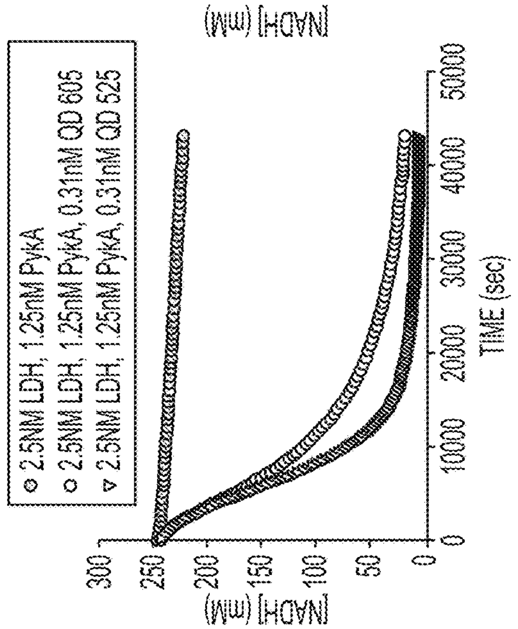
Figure 6A:
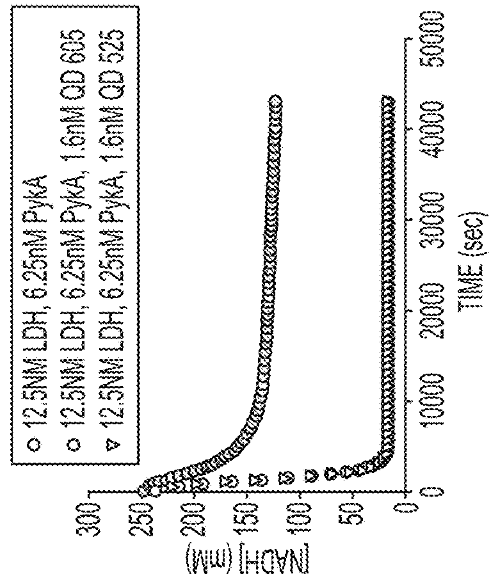
Figure 9A:
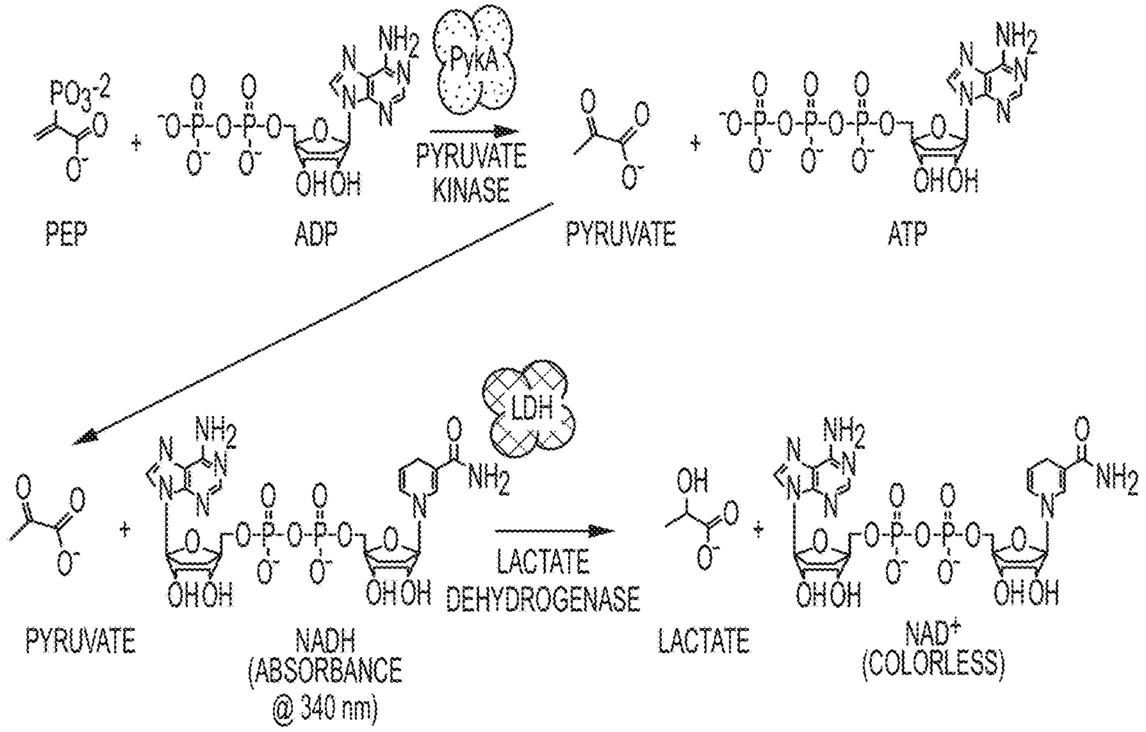
FIGS. 9A and 9B refer to combined reactions of pyruvate kinase and lactate dehydrogenase on a QD surface.
Figure 9B:
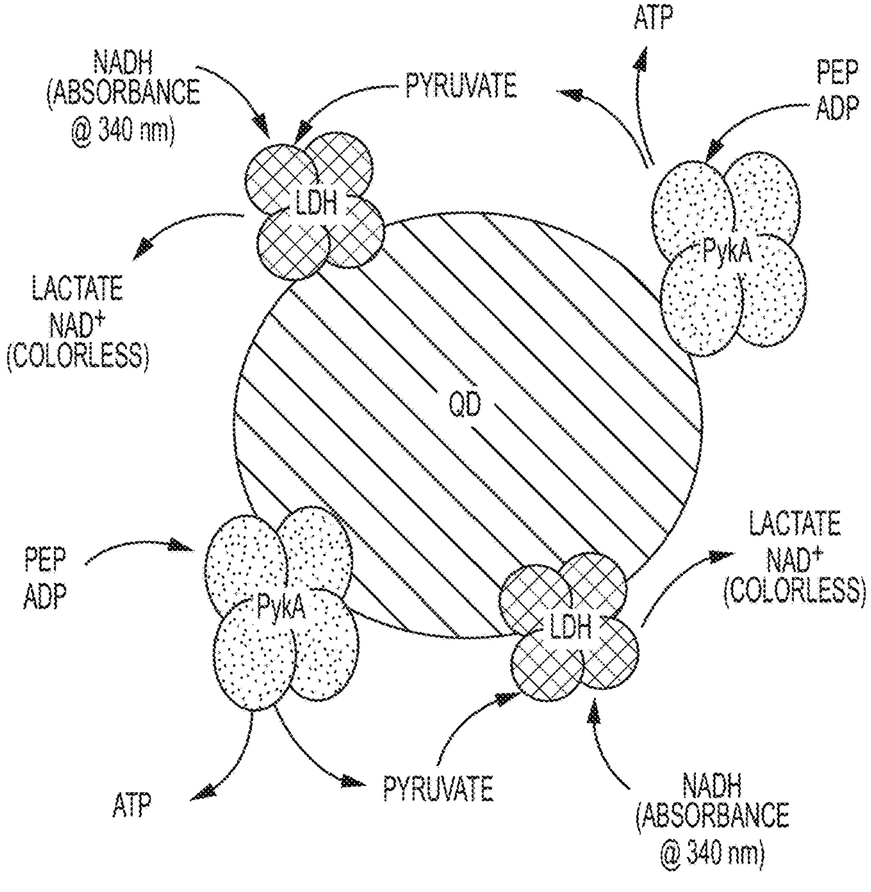
Figure 10:
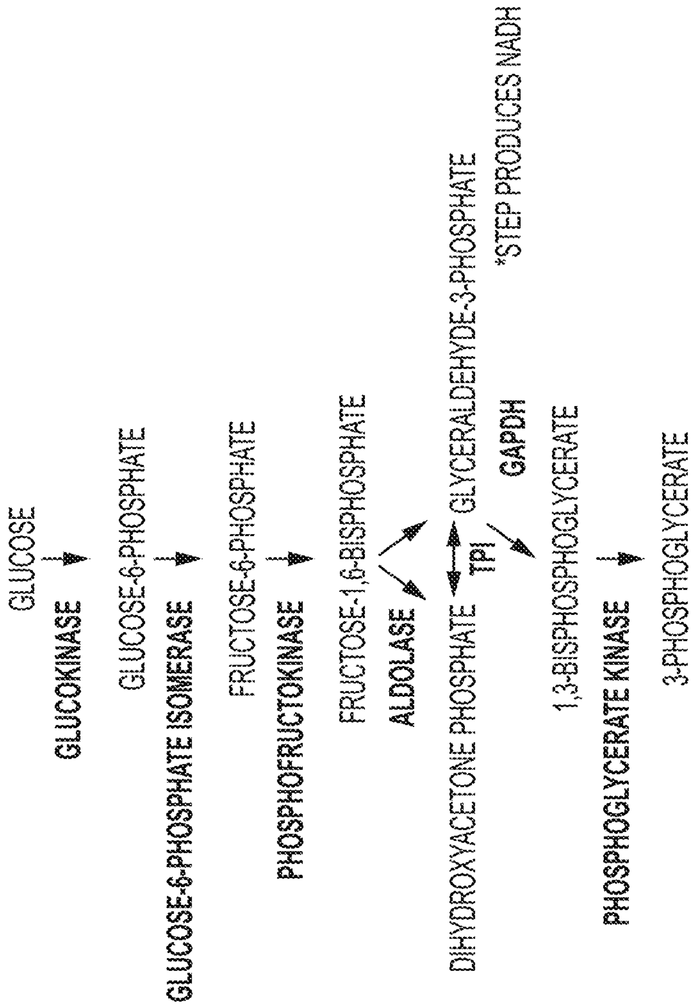
FIG. 10 illustrates a glycolytic pathway. This is a simplified scheme of the transformation of glucose into 3-phosphoglycerate by a 7 enzyme cascade. The product NADH is detected by assays and used to assess the overall pathway. The final enzyme, phosphoglycerate kinase, is an addition made in order to make the overall reaction thermodynamically favorable.

In a second example, the *E. coli* enzymes pyruvate kinase (PykA) and lactate dehydrogenase (LDH) were both expressed with N-terminal hexahistidine tags (FIG. 9). PykA's kinetics were diminished when bound to a QD (the first example of diminished enzyme kinetics at a QD surface observed herein), but LDH was activated tremendously (~60-fold). The cause of the large LDH activation appears to be caused by a stabilization of the LDH tetramer at low concentrations as a result of multiple monomers binding to the QD surface (FIG. 4). A gel-shift assay demonstrated that both enzymes appear to be capable of binding to a QD simultaneously (FIG. 5). When the enzymes were combined on the QD surface, enhanced initial rates of substrate turnover were observed (FIG. 6). Additionally, the enzymes on the QD appeared to be active at longer time points. This had a notable overall effect on product yield (particularly at lower enzyme concentrations), with the QD-bound enzymes completely turning over the available substrate whereas little to no substrate turnover was observed for unbound PykA and LDH. Furthermore, experiments were performed to attempt to disrupt substrate channeling (the passing of the product of one enzyme directly to another enzyme without its release into solution) by vigorous mixing of the QD-bound enzymes during catalysis. These stirred reactions showed slower overall kinetics compared to stationary reactions, suggesting that substrate channeling has a role to play in the pathway enhancement (FIG. 10). To exploit substrate channeling, embodiments can conduct a multi-enzyme reaction while minimizing any mixing or circulation of the reaction medium.

Figure 7:
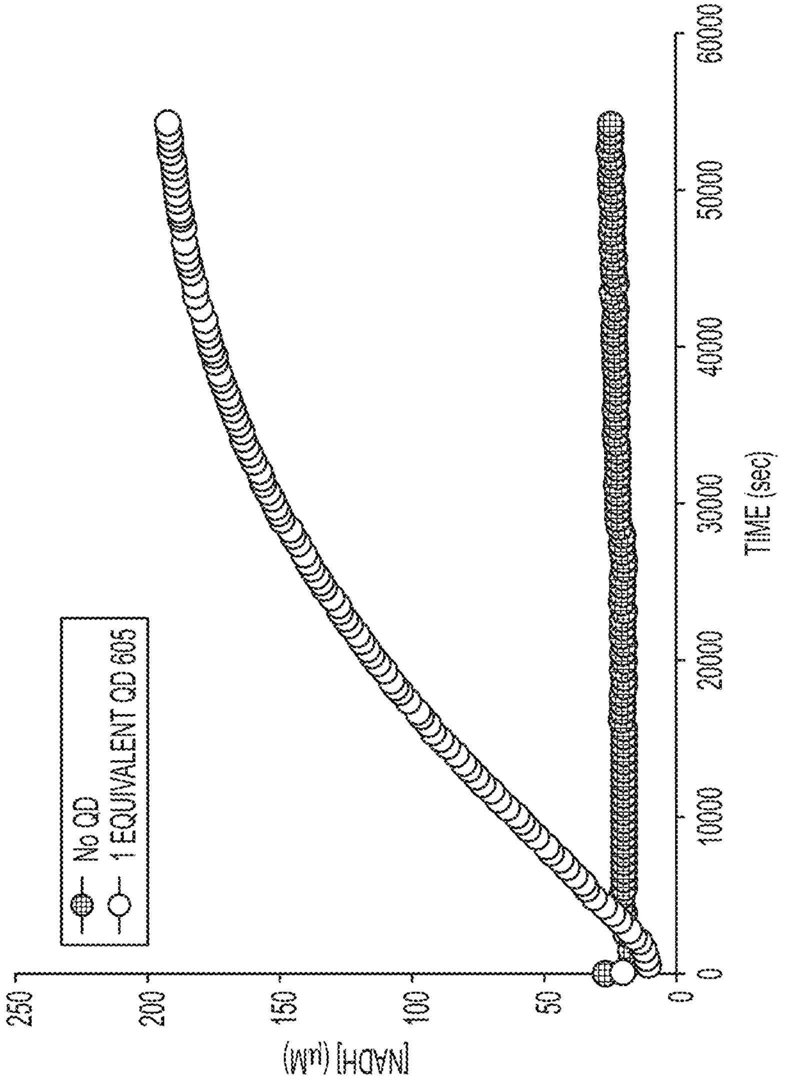
FIG. 7 shows the activity of a seven enzyme glycolytic cascade both with and without added QDs. Glucokinase, phosphoglucose isomerase, phosphofructokinase, fructose-bisphosphate aldolase, triosephosphate isomerase, glyceraldehyde-3-phosphoate dehydrogenase, and phosphoglycerate kinase were prepared and incubated either with or without QD. The kinetics were measured by monitoring the production of NADH over time under identical substrate concentrations.

In a third example, the use of collocation of enzymes of a QD surface was examined within a 7-enzyme cascade consisting of the enzymes glucokinase, phosphoglucose isomerase, phosphofructokinase, fructose-bisphosphate aldolase, triose phosphate isomerase, glyceraldehyde-3-phosphate dehydrogenase, and phosphoglycerate mutase, all of which were expressed and purified with hexahistidine tags (Scheme 3). When the enzymes are bound to a QD, production of NADH (the penultimate product of the pathway), was observed (FIG. 7). No product was observed in identical reactions lacking QDs.

The below table shows the enzymes used in the exemplary seven enzyme system and their ratios.

| Seven Enzyme System | Ratio of Enzyme/QD |
|---|---|
| Glucokinase (Glk) | 1.5 |
| Phosphoglucose isomerase (PGI) | 1.5 |
| Phosphofructokinase I (FPK) | 15.4 |
| Fructose-bisphosphate aldolase (FBA) | 23.5 |
| Triose phosphate isomerase (TPI) | 1.5 |
| Glyceraldehyde-3-phosphate dehydrogenase (GPD) | 15.4 |
| Phosphoglycerate kinase (PGK) | 0.4 |

In a fourth example, a nine enzyme system was prepared as described in the following table.

| Nine Enzyme System | Ratio of Enzyme/QD |
|---|---|
| Amylase (Amy) | 0.7 |
| Maltase (Mal) | 2.7 |
| Glucokinase (Glk) | 0.04 |
| Phosphoglucose isomerase (PGI) | 0.04 |
| Phosphofructokinase I (FPK) | 1.07 |
| Fructose-bisphosphate aldolase (FBA) | 1.07 |
| Triose phosphate isomerase (TPI) | 0.04 |
| Glyceraldehyde-3-phosphate dehydrogenase (GPD) | 1.07 |
| Phosphoglycerate kinase (PGK) | 0.17 |

Figure 11:
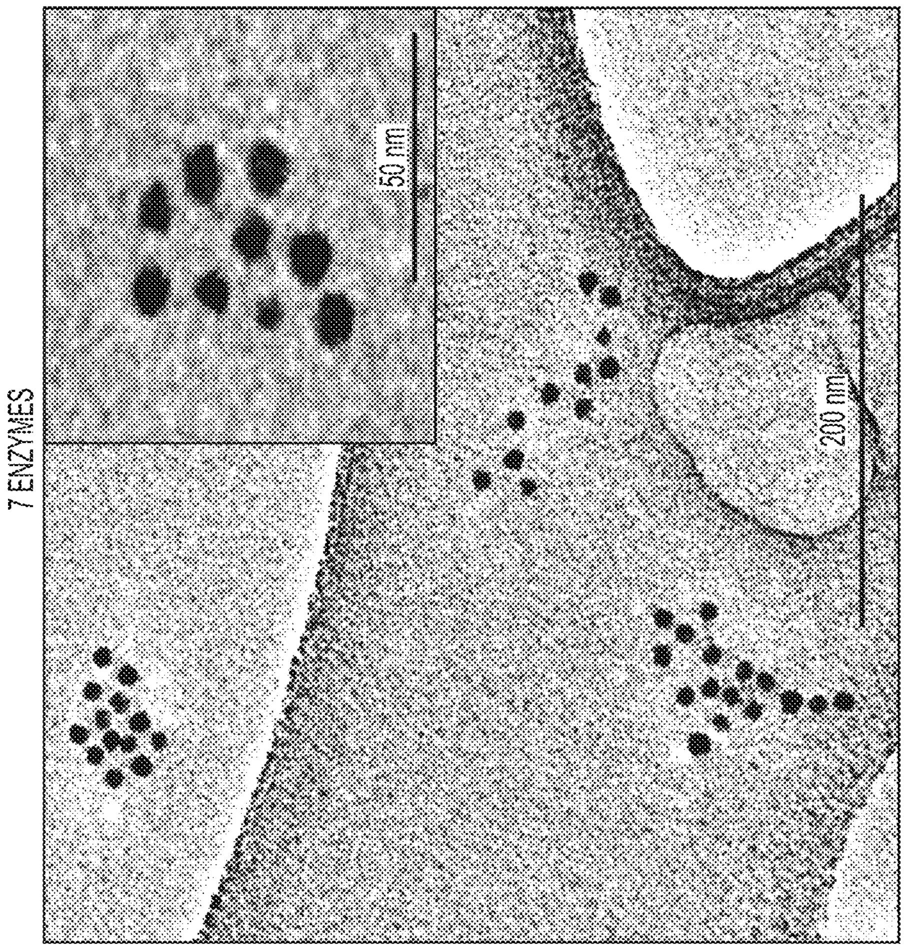
FIG. 11 is a transmission electron microscopy (TEM) micrograph showing the nanoclusters formed when 600 nm diameter QDs are assembled with the exemplary seven enzymes at the ratios indicated below. Analysis of the clusters indicated an average number of 9 QDs per cluster with a range from 3-14
Figure 12:
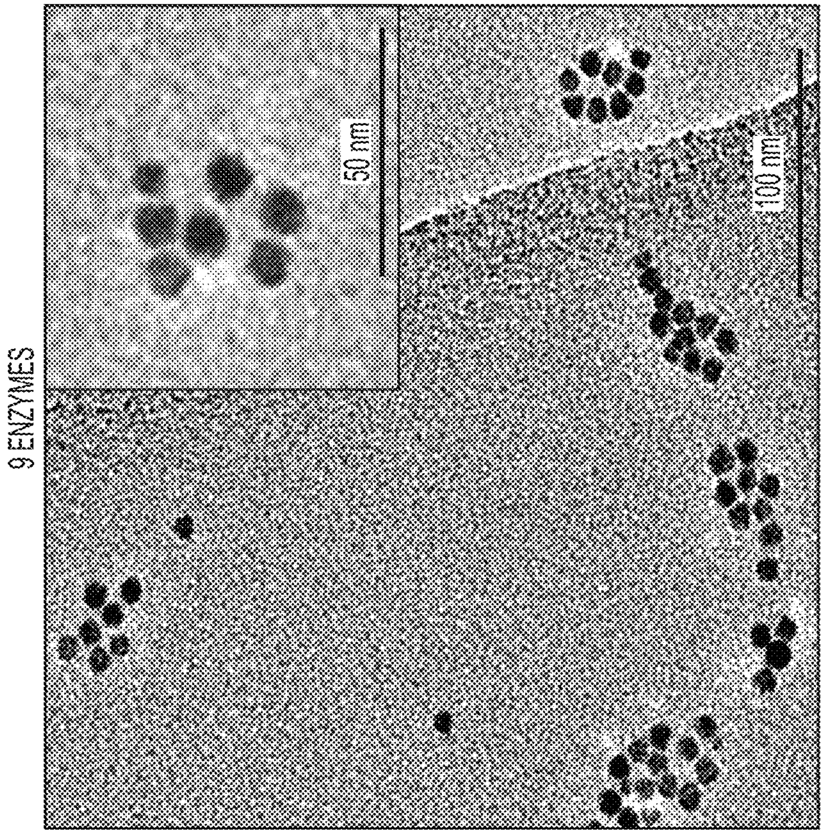
FIG. 12 is a TEM micrograph showing the nanoclusters formed when 600 nm diameter QDs are assembled with the exemplary nine enzymes at the ratios indicated below. Analysis of the clusters indicated an average number of less than 9 QDs per cluster (due to the smaller ratios of enzyme used) with a range from 1-14.

Assembly of the enzymes to the QDs formed nanoclustered structures (FIGS. 11 and 12) due to crosslinking between the QDs arising from the multiple $(His)_6$ present in the enzymes. These clusters of enzyme-decorated QDs, where on average, each nanoparticle is separated from the nearest neighboring nanoparticle by a distance of no more than about one nanoparticle diameter, appear to be critical to the channeled activity. The importance of such enzyme aggregates are believed to be critical to achieving channeling behavior regardless of the internal order of the enzymes as they promote dimensionally limited diffusion and significantly reduce intermediary escape in multistep enzyme catalytic process. See Section 4 of Rabe K S, Miller J, Skoupi M, Niemeyer C M. Cascades in Compartments: En Route to Machine-Assisted Biotechnology. Angew Chem Int Ed Engl. 2017 Oct. 23; 56(44):13574-13589. doi:10.1002/anie.201703806.

Figure 13:
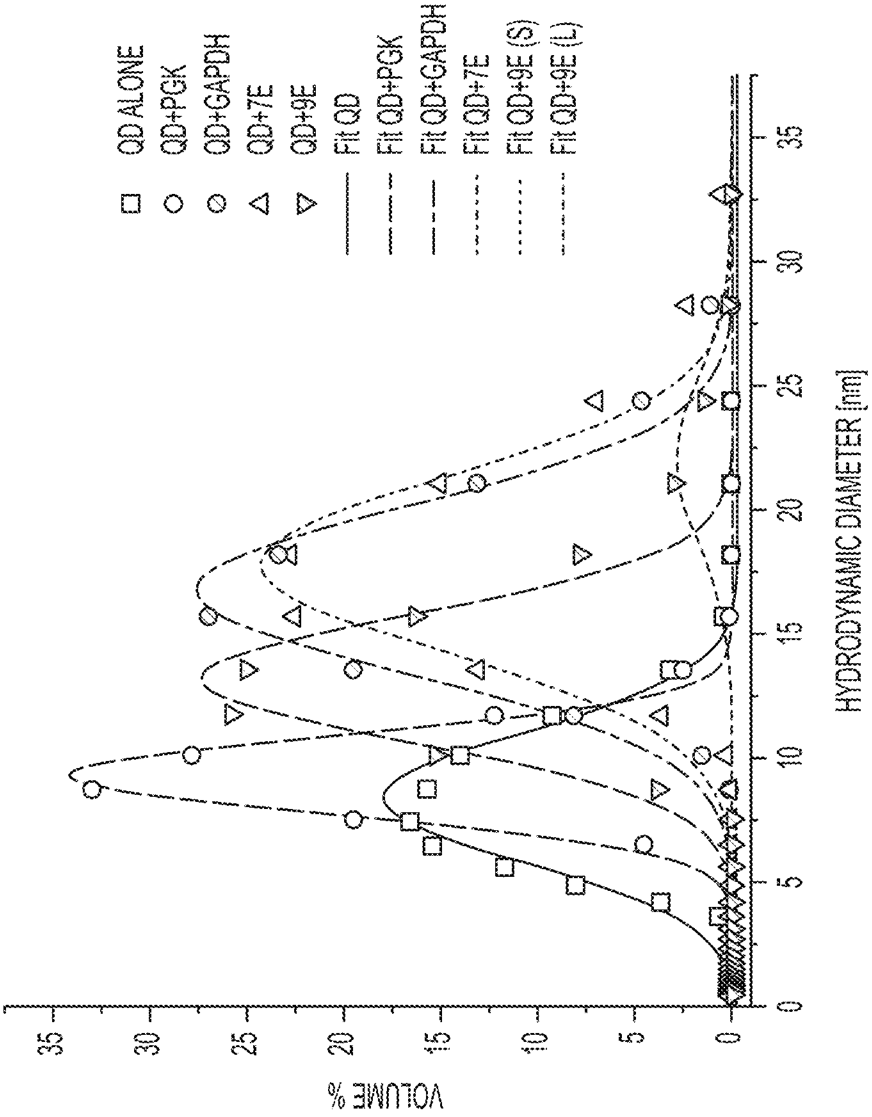
FIG. 13 is representative dynamic light scattering data from analyzing the cluster sizes formed when assembling the enzymes to the QDs. This, along with TEM data and other spectroscopic FRET data (not shown), was used to back estimate the average number of QDs per cluster in each configuration

FIG. 13 is Representative dynamic light scattering data from analyzing the cluster sizes formed when assembling the enzymes to the QDs. This, along with TEM data and other spectroscopic FRET data (not shown), was used to back estimate the average number of QDs per cluster in each configuration.

SUMMARY

Overall, these results indicate that NPs have the ability to enhance catalysis for multi-enzyme cascades when enzymes are attached to the NPs. The experiments with PykA and LDH demonstrate the power of co-localization of enzymes on a surface. Furthermore, the experiment in which separate assays were left stationary or vigorously mixed during catalysis supports the concept of substrate channeling on the NP surfaces. The addition of advection accelerates diffusion, thus disrupting any possible gradient of pyruvate near the NP surface. The observation that a stationary reaction produced faster kinetics suggests that such a gradient is present and is responsible for at least some of the enhanced catalytic rate. Finally, the experiment with the 7 glycolytic enzymes provides proof of concept that this strategy could be used for relatively large enzymatic cascades that rely on several different catalytic steps.

Advantages and Applications

Utilizing enzymes bound to metal-NPs to enhance the performance of an enzymatic cascade offers the following advantages:

(1) Metal-NPs can be easily functionalized with a wide variety of surface ligands that provide different surface charges, polarities, and steric bulk (2) Enzymes can be easily and tightly bound to the surface through a simple hexahistidine tag, which can be incorporated genetically into the enzymes of interest (3) The ability to site-specifically locate the hexahistidine tag on the enzyme allows for more uniform orientations of the enzymes on the surface (4) NP attachment can often enhance the activity of individual bound enzymes (5) Binding oligomeric enzymes to NPs via hexahistidine tags can stabilize the oligomeric structure at low concentrations and enhance activity (6) The enhanced activity of a bound enzyme can be harnessed in an enzymatic cascade, either with a bound or unbound enzyme partner (for example, the enzyme partner can be unbound if tests determine that it operates more effectively unbound than bound).

(7) The co-localization of enzymes on a NP allows for substrate channeling, thus further enhancing the kinetics of the reaction (8) Enzymes can be easily assembled on NPs in controlled ratios and controlled orientations (9) One can easily adjust the ratios of enzymes bound to a NP to tune the pathway for different catalytic rates and pathway optimization

(10) One can assemble custom enzymatic pathways that do not exist in nature and may generate products that would be toxic to a host organism.

(11) The large surface area of NPs allows for the conjugation of numerous enzymes to the surface

(12) Enzymes can be stabilized by binding to a NP surface

(13) Substrates/intermediates appear to accumulate near NP surfaces which may further facilitate substrate channeling between multiple bound enzymes

(14) If assembled on a magnetic NP, the magnetic NP could be used to remove material and or sequentially add the NP-enzymes to control and alter the chemistry.

Numerous industrial chemical reactions take advantage of enzymatic biocatalysis and enzyme immobilization methodologies. This technique has the potential to be used in such reactions since, contrary to most immobilization strategies, it enhances enzymatic activity (rather than resulting in a loss of activity), stabilizes the bound enzymes, and increases the kinetics of cascade reactions via what appears to be similar to a substrate channeling mechanism. The result is a more durable catalyst with a much improved total turn-over number.

In embodiments, the technique is used to conduct a cascade of enzyme-catalyzed reactions in a completely cell-free environment, with the reaction product(s) easily separated from the nanoparticle-bound enzymes.

Furthermore, the technique could be used for the enzymatic detection of metabolites and small molecules in clinical and other types of samples, by allowing for increased longevity of the enzymes and enhanced signal production rates. Thus, a wide variety of enzymatic assays might be improved.

Enzymes are currently used commercially in industry and pharmaceutical synthesis to catalyze various transformations, thus a NP-enzyme construct could serve in this role. Embodiments might have two, three, four, five, six, seven, eight, nine, ten, or more enzymes configured as a cascade where the product of a first enzyme is the substrate of a second enzyme, and so on.

CONCLUDING REMARKS

All documents mentioned herein are hereby incorporated by reference for the purpose of disclosing and describing the particular materials and methodologies for which the document was cited.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

REFERENCES

[1] Ansari, S. A., and Husain, Q. (2012) Potential applications of enzymes immobilized on/in nano materials: A review, *Biotechnology Advances* 30, 512-523.

[2] Blanco-Canosa, J. B., Wu, M., Susumu, K., Petryayeva, E., Jennings, T. L., Dawson, P. E., Algar, W. R., and Medintz, I. L. (2014) Recent progress in the bioconjugation of quantum dots, *Coordin Chem Rev* 263, 101-137.

[3] Breger, J. C., Ancona, M. G., Walper, S. A., Oh, E., Susumu, K., Stewart, M. H., Deschamps, J. R., and Medintz, I. L. (2015) Understanding How Nanoparticle Attachment Enhances Phosphotriesterase Kinetic Efficiency, *Acs Nano* 9, 8491-8503.

[4] Breger, J. C., Walper, S. A., Oh, E., Susumu, K., Stewart, M. H., Deschamps, J. R., and Medintz, I. L. (2015) Quantum dot display enhances activity of a phosphotriesterase trimer, *Chem Commun* 51, 6403-6406.

[5] Brown, C. W, Oh, E., Hastman, D. A., Walper, S. A., Susumu, K., Stewart, M. H., Deschamps, J. R., and Medintz, I. L. (2015) Kinetic enhancement of the diffusion-limited enzyme beta-galactosidase when displayed with quantum dots, *Rsc Adv* 5, 93089-93094.

[6] Claussen, J. C., Malanoski, A., Breger, J. C., Oh, E., Walper, S. A., Susumu, K., Goswami, R., Deschamps, J. R., and Medintz, I. L. (2015) Probing the Enzymatic Activity of Alkaline Phosphatase within Quantum Dot Bioconjugates, *J Phys Chem C* 119, 2208-2221.

[7] Es, I., Vieira, J. D. G., and Amaral, A. C. (2015) Principles, techniques, and applications of biocatalyst immobilization for industrial application, *Appl Microbiol Biot* 99, 2065-2082.

[8] Fu, J. L., Liu, M. H., Liu, Y, Woodbury, N. W., and Yan, H. (2012) Interenzyme Substrate Diffusion for an Enzyme Cascade Organized on Spatially Addressable DNA Nanostructures, *J Am Chem Soc* 134, 5516-5519.

[9] Johnson, B. J., Algar, W R., Malanoski, A. P., Ancona, M. G., and Medintz, I. L. (2014) Understanding enzymatic acceleration at nanoparticle interfaces: Approaches and challenges, *Nano Today* 9, 102-131.

[10] Sapsford, K. E., Pons, T., Medintz, I. L., Higashiya, S., Brunel, F. M., Dawson, P. E., and Mattoussi, H. (2007) Kinetics of metal-affinity driven self-assembly between proteins or peptides and CdSe—ZnS quantum dots, *J Phys Chem C* 111, 11528-11538.

What is claimed is:

1. A method of conducting a cascade reaction, comprising:

providing a cascade cluster comprising a plurality of nanoparticles associated together as a cluster, wherein each nanoparticle is bound to a plurality of enzymes configured as an enzymatic cascade wherein the product of a first enzyme is the substrate of a second enzyme and so forth, wherein the enzymatic cascade comprises at least two different enzymes, and wherein the nanoparticles in the cluster are closely associated with one another such that, on average, each nanoparticle is separated from the nearest neighboring nanoparticle by a distance of no more than about one nanoparticle diameter;

contacting the cascade cluster with a substrate of the first enzyme; and allowing a reaction to proceed so that each of the plurality of enzymes acts in succession to produce an end product, wherein the reaction is performed while minimizing stirring or mixing and;

wherein at least one of the enzymes comprises multiple polyhistidine tags acting to cross-link the nanoparticles into the cluster.

2. The method of claim 1, wherein the nanoparticle is a quantum dot and the enzymes are bound to the quantum dot via polyhistidine sequences in the enzymes.

3. The method of claim 1, wherein said plurality of enzymes comprises pyruvate kinase (PykA) and lactate dehydrogenase (LDH).

4. The method of claim 1, wherein said plurality of enzymes comprises glucokinase, phosphoglucose isomerase, phosphofructokinase, fructose-bisphosphate aldolase, triose phosphate isomerase, glyceraldehyde-3-phosphate dehydrogenase, and phosphoglycerate mutase.

* * * * *